US008558878B2

(12) United States Patent
Bousquet et al.

(10) Patent No.: US 8,558,878 B2
(45) Date of Patent: Oct. 15, 2013

(54) STEERABLE STRUCTURE OF CATHETER OR ENDOSCOPE TYPE

(75) Inventors: Sadia Bousquet, Moissy Cramayel (FR); Jerome Szewczyk, Vienne en Arthies (FR)

(73) Assignees: SNECMA, Paris (FR); Centre National de la Recherche Scientifique, Paris (FR); Universite Pierre et Marie Curie, Paris (FR)

( * ) Notice: Subject to any disclaimer, the term of this patent is extended or adjusted under 35 U.S.C. 154(b) by 1204 days.

(21) Appl. No.: 12/235,148

(22) Filed: Sep. 22, 2008

(65) Prior Publication Data

US 2009/0079821 A1 Mar. 26, 2009

(30) Foreign Application Priority Data

Sep. 26, 2007 (FR) ...................................... 07 06726

(51) Int. Cl.
*A62B 1/04* (2006.01)

(52) U.S. Cl.
USPC ............................................. 348/65; 600/101

(58) Field of Classification Search
USPC ...................... 348/65; 600/101–151; 310/330
See application file for complete search history.

(56) References Cited

U.S. PATENT DOCUMENTS

| | | | | |
|---|---|---|---|---|
| 5,279,559 A | * | 1/1994 | Barr ............................ | 604/95.05 |
| 5,484,424 A | * | 1/1996 | Cottenceau et al. .......... | 604/525 |
| 5,487,757 A | * | 1/1996 | Truckai et al. ................ | 604/264 |
| 5,531,664 A | * | 7/1996 | Adachi et al. ................. | 600/149 |
| 5,624,380 A | * | 4/1997 | Takayama et al. ............ | 600/146 |
| 5,679,216 A | * | 10/1997 | Takayama et al. ............ | 438/598 |
| 5,810,717 A | * | 9/1998 | Maeda et al. ................. | 600/151 |
| 5,827,272 A | * | 10/1998 | Breining et al. ............... | 606/41 |
| 5,846,247 A | * | 12/1998 | Unsworth et al. ............ | 606/108 |
| 6,203,494 B1 | * | 3/2001 | Moriyama ..................... | 600/144 |
| 6,240,231 B1 | | 5/2001 | Ferrera et al. | |
| 6,245,053 B1 | * | 6/2001 | Benjamin ...................... | 604/523 |
| 6,425,418 B1 | * | 7/2002 | Maeda et al. ................. | 138/133 |
| 6,488,631 B2 | * | 12/2002 | Ohara et al. .................. | 600/462 |
| 6,574,958 B1 | * | 6/2003 | MacGregor .................... | 60/527 |
| 6,672,338 B1 | * | 1/2004 | Esashi et al. .................. | 138/119 |
| 2002/0062083 A1 | * | 5/2002 | Ohara et al. .................. | 600/462 |
| 2002/0142119 A1 | * | 10/2002 | Seward et al. ............... | 428/36.9 |
| 2003/0093106 A1 | * | 5/2003 | Brady et al. .................. | 606/194 |
| 2004/0106853 A1 | * | 6/2004 | Moriyama ..................... | 600/140 |
| 2004/0193013 A1 | * | 9/2004 | Iwasaka et al. ............... | 600/140 |
| 2006/0009785 A1 | * | 1/2006 | Maitland et al. .............. | 606/113 |
| 2006/0064055 A1 | * | 3/2006 | Pile-Spellman et al. ... | 604/95.05 |
| 2006/0183977 A1 | * | 8/2006 | Ishigami et al. .............. | 600/179 |

FOREIGN PATENT DOCUMENTS

EP 0 554 128 A1 8/1993
WO WO 2004/084714 A1 10/2004

* cited by examiner

*Primary Examiner* — El Hadji Sall
(74) *Attorney, Agent, or Firm* — Oblon, Spivak, McClelland, Maier & Neustadt, L.L.P.

(57) ABSTRACT

A steerable structure of the catheter or endoscope type is disclosed. The structure includes an elastically or deformable longitudinal body including at least one actuator of material of the shape memory type incorporated longitudinally with the body together with a Joule-effect heater enabling the actuator to be contracted longitudinally in order to cause the longitudinal body to bend. The actuator extends over at least one portion of the body that presents varying stiffness.

20 Claims, 4 Drawing Sheets

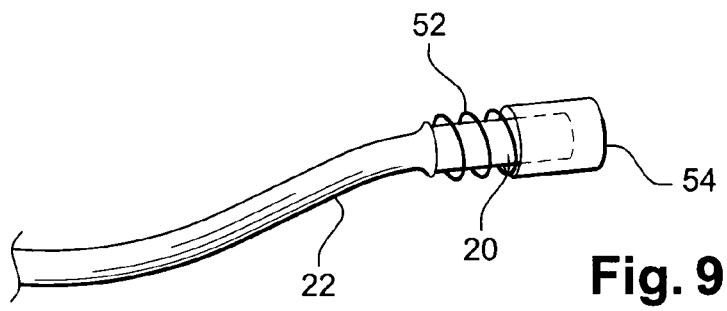
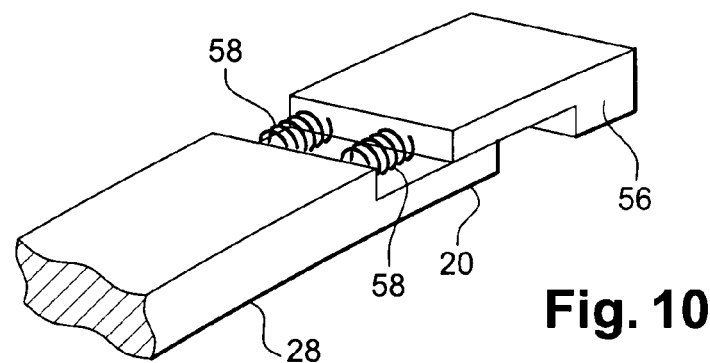
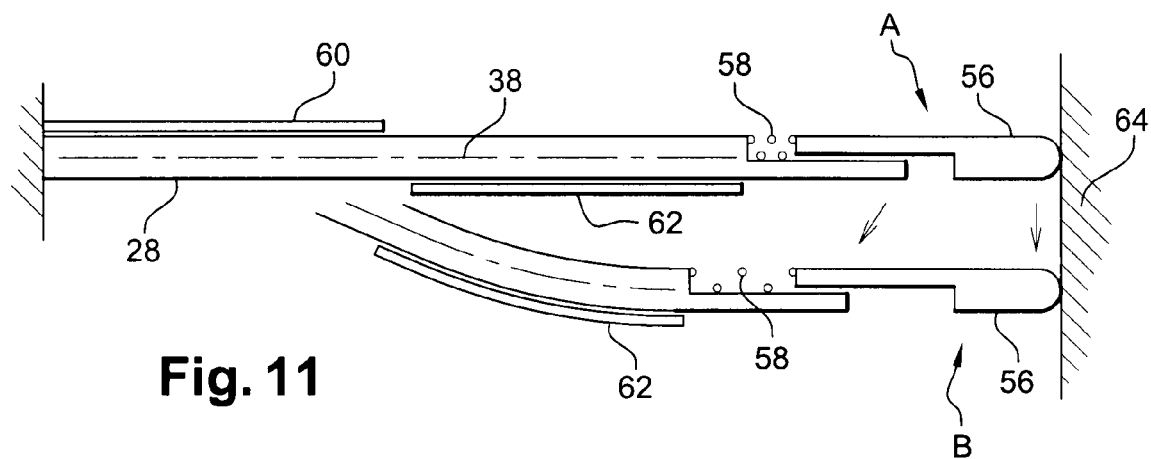

STEERABLE STRUCTURE OF CATHETER OR ENDOSCOPE TYPE

The present invention relates to a steerable structure of catheter or endoscope type for internally investigating a three-dimensional system, such as a turbomachine, for example.

TECHNOLOGICAL BACKGROUND OF THE INVENTION

Present catheters or endoscopes are in the form of long tubes that are rigid or elastically deformable and that have an end that is steerable relative to a longitudinal axis of the tube so as to enable a particular viewing angle to be selected and so as to facilitate advancing the catheter or endoscope.

In order to curve a particular zone of the catheter or the endoscope appropriately, it is known to place actuators along its structure, which actuators are in the form of wires made of shape memory material, which wires are connected to Joule-effect heater means. Such actuators shrink in length under the effect of an increase in temperature thereby changing the curvature of the catheter or endoscope in the zones where the actuators are located. Controlling the various actuators distributed along the length of the endoscope or catheter enables its distal end to be positioned in three-dimensional space.

Nevertheless, that type of device presents several drawbacks. The diameter of the distal end is generally of the order of 5 millimeters (mm) to 8 mm so as to avoid bending under the effect of gravity. That excessive end diameter makes it impossible to investigate certain critical zones. In order to obtain the angular orientation desired for the end of the catheter or endoscope, it is necessary to modify parameters such as the length and the diameter of the actuator wires, and that is lengthy and complicated. Present devices also suffer from limitations due mainly to lack of mobility and maneuverability in places that are geometrically complex or cramped. During contraction of an actuator, bending locally gives the device a radius of curvature that is substantially constant since the stiffness of the device is substantially constant all along its length. Under such circumstances, it is not possible to inspect three-dimensional cavities of complex shape having passages of small dimensions and requiring a plurality of successive changes of orientation.

As a result, certain zones in a machine can remain inaccessible even though it is desired to perform conventional non-destructive inspection thereof, such as inspection performed using Foucault currents or ultrasound, given the complexity of access and of routing, and given the small dimensions of the passages to be followed. Finally, those known devices are not suitable for being controlled automatically, thereby correspondingly complicating the investigation procedure since it needs to be performed manually.

SUMMARY OF THE INVENTION

An object of the present invention is to provide a structure of the above-described type that avoids the above-mentioned drawbacks of the prior art in a manner that is simple, effective, and inexpensive, giving access to portions of a system that are inaccessible using known means.

To this end, the invention provides a steerable structure of catheter or endoscope type for observing or treating a masked object that is accessible via a passage that is narrow and/or sinuous, the structure comprising an elastically deformable longitudinal body having at least one actuator of shape memory type material incorporated longitudinally in the longitudinal body together with Joule-effect heater means enabling the actuator to be contracted longitudinally so as to cause the longitudinal body to bend, wherein the actuator extends over at least one portion of the longitudinal body that presents varying stiffness.

According to the invention, the varying stiffness of the longitudinal body thus enables bending to be small in zones where stiffness is large and bending to be greater in zones where stiffness is smaller, thereby making it possible to obtain a curved profile for the structure that includes radii of curvature that vary along the length of the structure.

By causing the stiffness of the portion of the structure carrying the actuator to be adapted to the curvature that is desired, it is possible to impose the angular orientation on the distal end of the structure more simply and more accurately than in the prior art.

According to another characteristic of the invention, the portion of the structure that is of varying stiffness includes at least one extra thickness of material, thereby enabling stiffness to be increased in that zone compared with zone not including extra thickness, and thus making it possible, when the actuator contracts, to obtain a profile with a varying radius of curvature.

The varying stiffness of the longitudinal body can be designed so that contraction of the actuator gives rise to modification and/or inversion of the longitudinal or transverse curvature of the longitudinal body.

The longitudinal body and the extra thickness may be made of similar materials, such as for example one or more polymers.

In an embodiment, the longitudinal body comprises at least one tube having a diameter of about 2 mm to 6 mm, the actuator extending longitudinally over an inside wall or an outside wall of the tube, over at least a fraction of its length.

In another variant embodiment, the longitudinal body comprises a blade of elongate cross-section, and two parallel actuators are incorporated with the blade and extend along a longitudinal face of the blade. The blade may present thickness of about 1 mm to 2 mm, width of about 1 centimeter (cm), and length of about 5 cm to 10 cm.

In systems such as turbomachines, the zones that are to be investigated present a high degree of axial symmetry. As a result, the passages to be followed by the structure are often sections of small height but large width, such that it is possible to envisage using structures of elongate cross-section, e.g. of rectangular cross-section. The use of a structure of such a shape makes it possible to pass additional tools, such as clips, optical fibers, various connections, or the like, through channels that extend longitudinally in the structure. In addition, a structure of elongate cross-section is better at withstanding transverse stresses applied in the direction of the large dimension of said section.

The number of actuators may also be increased because of the greater amount of room available in the cross-section, thereby enabling better control to be obtained over the curvature given to the structure.

The actuator used for bending the endoscope may be a wire of titanium and nickel alloy presenting a diameter of about 0.1 mm to 0.5 mm.

More generally, it is possible to use actuators of materials presenting the property of contracting and shortening in length when being heated, and in particular materials such as those known as shape memory materials.

According to another characteristic of the invention, the structure is of the telescopic type and comprises a plurality of elastically deformable bodies provided with actuators and engaged in one another.

Advantageously, the structure includes, at its distal end, resilient means that exert a longitudinal thrust force and that are connected to a head provided with non-destructive inspection means.

In this configuration, the distal end of the structure is not rigidly connected to the elastically deformable body, but is connected thereto via thrust means that enable continuous contact to be ensured between the surface of the part under inspection and the non-destructive inspection means carried by the head of the structure.

The thrust means may be helical springs, including some made of contractile material and connected to Joule-effect heater means.

The use of springs made of contractile material enables the stiffness of the spring to be varied so as to better adjust the pressure exerted on the surface of the part under inspection.

The non-destructive inspection means may be Foucault current probes or ultrasound probes, for example.

One transverse dimension of the structure may vary from about 8 mm at its proximal end to about 1 mm at its distal end. Such a structure may include means for hanging on or bearing against surrounding stationary elements.

Advancing the structure inside a system, by successively engaging a plurality of individual steerable structures one in another can lead to the distal end thereof being moved by the structure bending. The engagement or bearing means then make it possible to take up an accurate position against intermediate stationary elements so as to limit the effect of gravity on the structure and improve control over the positioning and the orientation of its end. This also makes it possible to provide catheter or endoscope type structures that are longer and finer.

The means for electrically supplying the actuators inducing heating of the actuators, can be controlled automatically, making it possible, when investigating a system of known geometry, to cause the structure to move inside the system being investigated automatically, thereby avoiding numerous difficulties inherent to continuously controlling actuators based on contractile material.

BRIEF DESCRIPTION OF THE DRAWINGS

The invention can be better understood and other details, advantages, and characteristics of the invention appear on reading the following description given by way of non-limiting example with reference to the accompanying drawings, in which:

FIGS. 9 and 10 are diagrammatic perspective views of structures including thrust springs at their distal ends;

FIG. 11 is a diagrammatic axial section view of a steerable structure of varying stiffness having a distal end that includes thrust springs.

DETAILED DESCRIPTION

Figure 1:
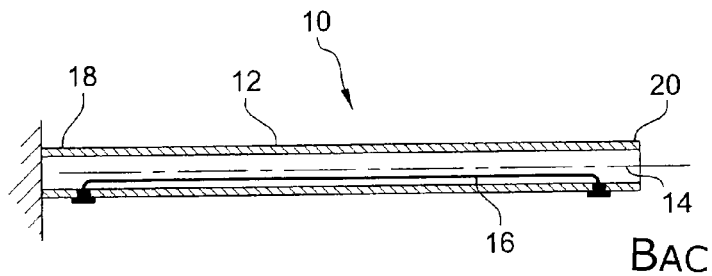
FIG. 1 is a diagrammatic axial section view of a prior art steerable tubular structure including an actuator made of contractile-material.

Reference is first made to FIG. 1 which is a diagrammatic view of a steerable structure 10 of the catheter or endoscope type according to the prior art and comprising a tubular flexible body 12 of longitudinal axis 14 and including an actuator 16 of contractile material, e.g. of the shape memory alloy (SMA) type disposed along the tubular structure and inside it. This actuator 16 is in the form of a wire connected to electrical power supply means (not shown). The steerable structure 10 has a stationary proximal end 18 and a steerable distal end 20.

Figure 2:
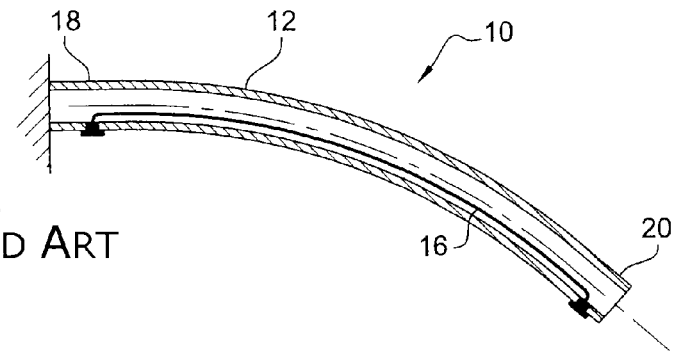
FIG. 2 is a diagrammatic axial section view of the structure shown in FIG. 1, the structure being curved by heating the contractile material.

Heating the SMA by the Joule effect induces a rearrangement of the atoms constituting the wire (when the activation temperature is reached), leading to contraction (with a response time of less than one second) and thus to a reduction in its length. The wire 16 fastened to a wall of the tube 12 induces bending of its distal end 20 in a direction perpendicular to the axis 14 (FIG. 2). The structure 10 as bent in this way adopts a circularly-arcuate profile with a radius of curvature that is substantially constant insofar as stiffness along the tube 12 is substantially constant. If it is necessary to limit the relative lateral movement between the two ends 18 and 20 of the catheter, such a catheter enables the distal end 20 to be steered angularly away from the longitudinal axis 14 through only a few degrees. A greater change in angular orientation will lead to an increase in the lateral movement of the distal end 20 of the catheter. Such a structure can therefore be used only in systems having narrow passages and requiring only small angular modification, or else in systems having passages that are large enough to allow a large amount of lateral movement, thereby constituting a severe limitation on the extent to which it is possible to investigate the insides of systems that are very complex and cramped, as are to be found in aeronautic, for example.

Stopping the Joule-effect heating of the wire leads to the wire 16 cooling and to the structure 10 returning to its initial longitudinal state by elastic effect.

Figure 3:
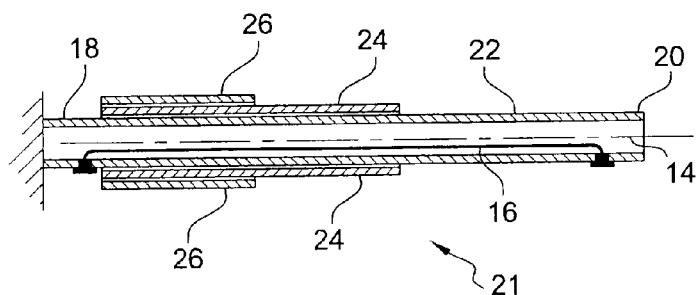
FIG. 3 is a diagrammatic axial section view of a steerable tubular structure of variable stiffness according to the invention.

In the invention, and as shown in Fig. 3, the structure 21 comprises a flexible body 22 having at least one portion of varying stiffness over which the SMA wire 16 extends. This variation in stiffness is obtained by installing or forming extra thicknesses of material on the outside surface of the tube 22. In the example shown, a first extra thickness of material 24 is disposed around the tube 22 and then a second extra thickness 26 of shorter axial dimension than the first is placed around the first extra thickness 24. Thus, the flexible body presents stiffness that decreases going from its proximal end 18 towards its distal end 20.

Figure 4:
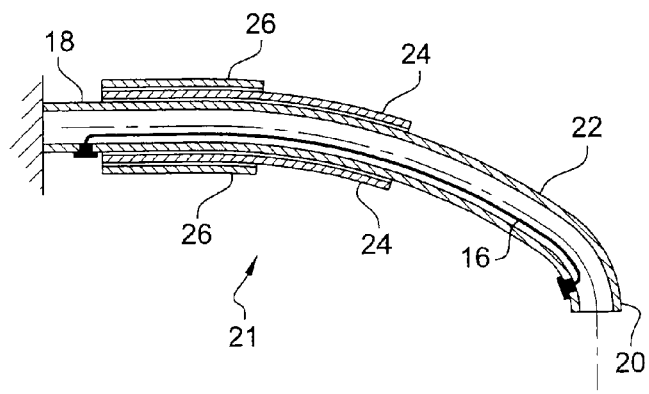
FIG. 4 is a diagrammatic view of the tubular structure of FIG. 3, the tubular structure being curved by heating the contractile material.

During contraction of the wire 16 by Joule-effect heating, the tube is bent about a radius of curvature that varies (FIG. 4). The tube curves little in its portion presenting great stiffness and it curves to a greater extent in the zone of lower stiffness. It can also be seen that its lateral movement is smaller and thus, compared with the prior art, less space is occupied for given angular steering of the distal end 20.

It is thus possible to obtain changes in the steering of the distal end of up to 90° from the longitudinal axis 14 with a small amount of lateral movement. This can be achieved insofar as the tube 22 does not present a diameter that is too great relative to the dimensions of the SMA wire 16.

Typically, the diameter of the wire 16 is of the order of 0.5 mm to 0.1 mm and it is caused to contract longitudinally by being heating by the Joule effect (produced by electrical power of about 0.5 watts (W)), where said contraction is of the order of 5% to 6% of its length. The tube 22 has a diameter of about 2 mm to 6 mm and it is made of polymer material, like existing medical catheters. Adjusting the magnitude of the electric current conveyed in the actuators can thus serve to adjust contraction and hence the curvature of the body 22.

Figure 5:
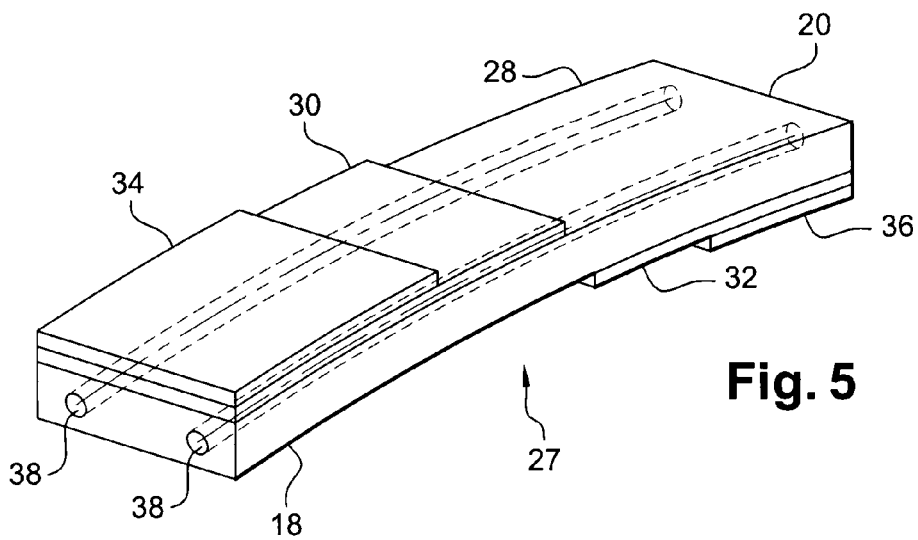
FIG. 5 is a diagrammatic perspective view of a structure of elongate cross-section and variable stiffness.

The passages taken by endoscopes or catheters for inspecting machines are often in the form of narrow slots, in particular in systems that present axial symmetry such as turbomachines. There is therefore no need for the catheter to be tubular and it may have some other shape. The invention can thus be applied equally well to a longitudinal flexible body 28 of elongate cross-section as shown in FIG. 5, where the body 28 is in the form of a blade of substantially rectangular section.

In a manner similar to the above-described embodiment, the catheter 27 comprises a flexible body 28 made up of layers of material disposed as extra thicknesses so as to modify the stiffness of the blades in the longitudinal direction. The additional layers of material are formed by strips that are likewise of rectangular section. The structure in this example has four layers of material or added strips, of width identical to the width of the blade 28. A first strip 30 is positioned on one face of the body 28 while another strip 32 having the same length as the first is positioned on its opposite face, at the other end of the longitudinal body 28. Two other strips 34, 36 having the same length are disposed respectively on each of the first two strips 30 and 32, and are of lengths that are shorter than the strips 30 and 32.

Two SMA or contractile parallel wires 38 are incorporated in the blade 28 and extend parallel to its longitudinal faces in its midplane.

Figure 6:
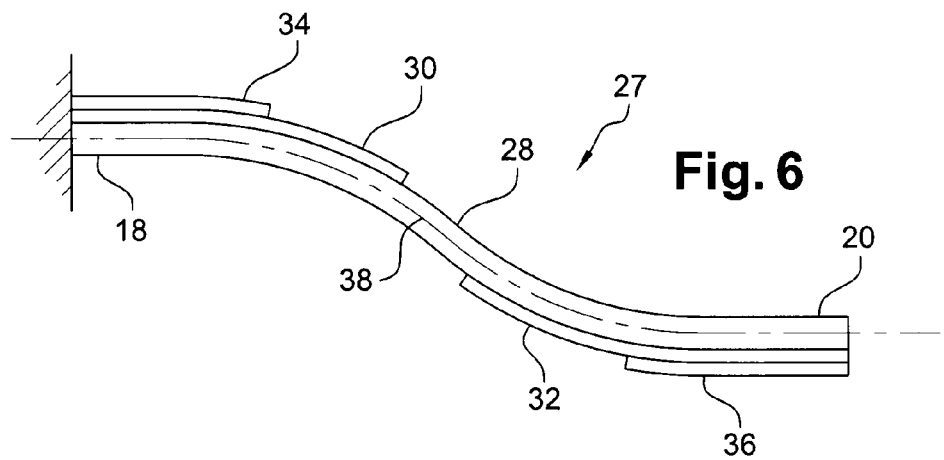
FIG. 6 is a view of the structure of FIG. 5, the structure being curved by heating the contractile material.

By heating the wires 38 by the Joule effect, a curved structure is obtained that is S-shaped (FIG. 6), since on going from the proximal end 18 to the distal end 20 of the longitudinal body, stiffness decreases, and is then constant on one face of the blade 28, and varies inversely on the other face. This structure is particularly useful when it is needed to offset the distal end 20, perpendicularly to the longitudinal axis, but without changing its angular orientation, or more generally when it is necessary not only to change the curvature of the longitudinal body, but also to reverse it in some particular zone.

Figure 7:
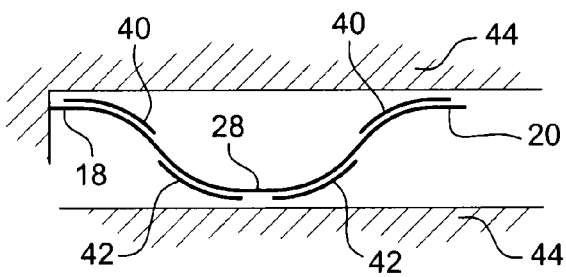
FIGS. 7 and 8 are diagrammatic axial section views of structures curved respectively into an S-shape and into a hook shape according to the invention.

The structure of FIG. 7 presents a dish-shape. Such a shape can be obtained by adding a strip 40 of extra thickness to the flexible body 28 at each of its ends, these two strips being placed on the same face, while its opposite face carries two strips 42 aligned along the body 28 and disposed between the end strips 40. This type of structure can be used in order to stabilize an endoscope or a catheter by bearing against surrounding stationary elements 44, thereby limiting the effects of gravity on the structure as a whole and making it possible to use catheters that are longer and finer than would be possible if they were made up solely of self-supporting structures. Hanging or bearing means can also be particularly useful during a non-destructive inspection operation as described below that requires the distal end 20 of the catheter to have a position that is stable.

Figure 8:
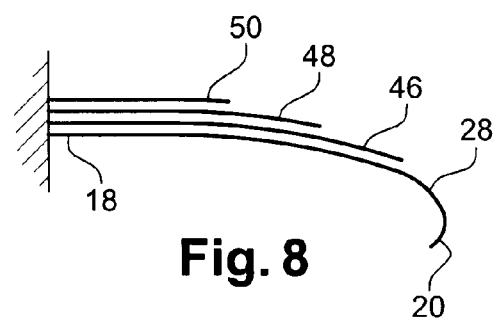

The hook-shaped structure of FIG. 8 can be obtained by using three layers of material 46, 48, and 50 of different lengths that are stacked on one another on a single face of the blade 28. Thus, the proximal end 18 of the longitudinal body 28 bends only a little, while the majority of the bending is concentrated at its distal end 20, thereby enabling the distal end 20 to be moved through an angle that can be greater than 90° while maintaining a lateral movement that is small.

As shown in FIGS. 9 and 10, catheters or endoscopes may include resilient means exerting a longitudinal thrust force on a head that is provided with non-destructive inspection means. These resilient means may be constituted, for example, by helical springs.

With an endoscope or catheter that is tubular (FIG. 9) a helical spring 52 is disposed around the distal end 20 of the flexible body 22 and bears against a rim on the longitudinal body 22, with the other end of the spring 52 bearing against the end of a cap-forming element 54 that surrounds the spring 52.

When the flexible body 28 (FIG. 10) is of elongate cross-section, e.g. of rectangular cross-section, its distal end 20 may include a rectangular step over which a head 56 of complementary shape is guided. The head 56 is connected to the longitudinal body 28 by two springs 58 arranged in parallel.

When the catheter is brought close to the surface of a part of interest, the springs 52, 58 enable the head 54, 56 to be kept in contact with the surface for the time required for examining the part by using the non-destructive inspection means.

The springs 52, 58 may be made of shape memory or contractile material when inspecting the stiffness of the spring or the applied force is of interest. Such springs can also be used for accurately controlling the distance between the end of the head and the surface.

FIG. 11 shows two positions of a catheter or endoscope of the invention, one of the positions (A) corresponding to an initial state prior to elastic deformation, and the other position (B) corresponding to a state after elastic deformation. The catheter is of the type having an elongate cross-section and it comprises two layers of material 60, 62 placed on opposite faces at the ends of the flexible body 28 and two SMA wires 38 as described in FIG. 5, together with one or more springs 58 connecting the head 56 to the flexible body 28, the head 56 being in contact with a surface of the part of interest 64.

During Joule-effect heating, the catheter takes up an S-shape according to the above-described principle, thereby enabling the distal end to be moved perpendicularly to the longitudinal axis without changing its orientation. The function of the spring(s) 58 is to keep the head permanently in contact with the surface of the part 64.

By means of this device and by placing non-destructive inspection means in the head 56, it is possible to investigate the inside of the part 64 by scanning, with the head 56 being caused to perform straight-line movement by repeated actuation of the SMA wires 38.

Non-destructive inspection means such as Foucault current probes or ultrasound probes can be particularly useful in detecting surface cracks.

Figure 12:
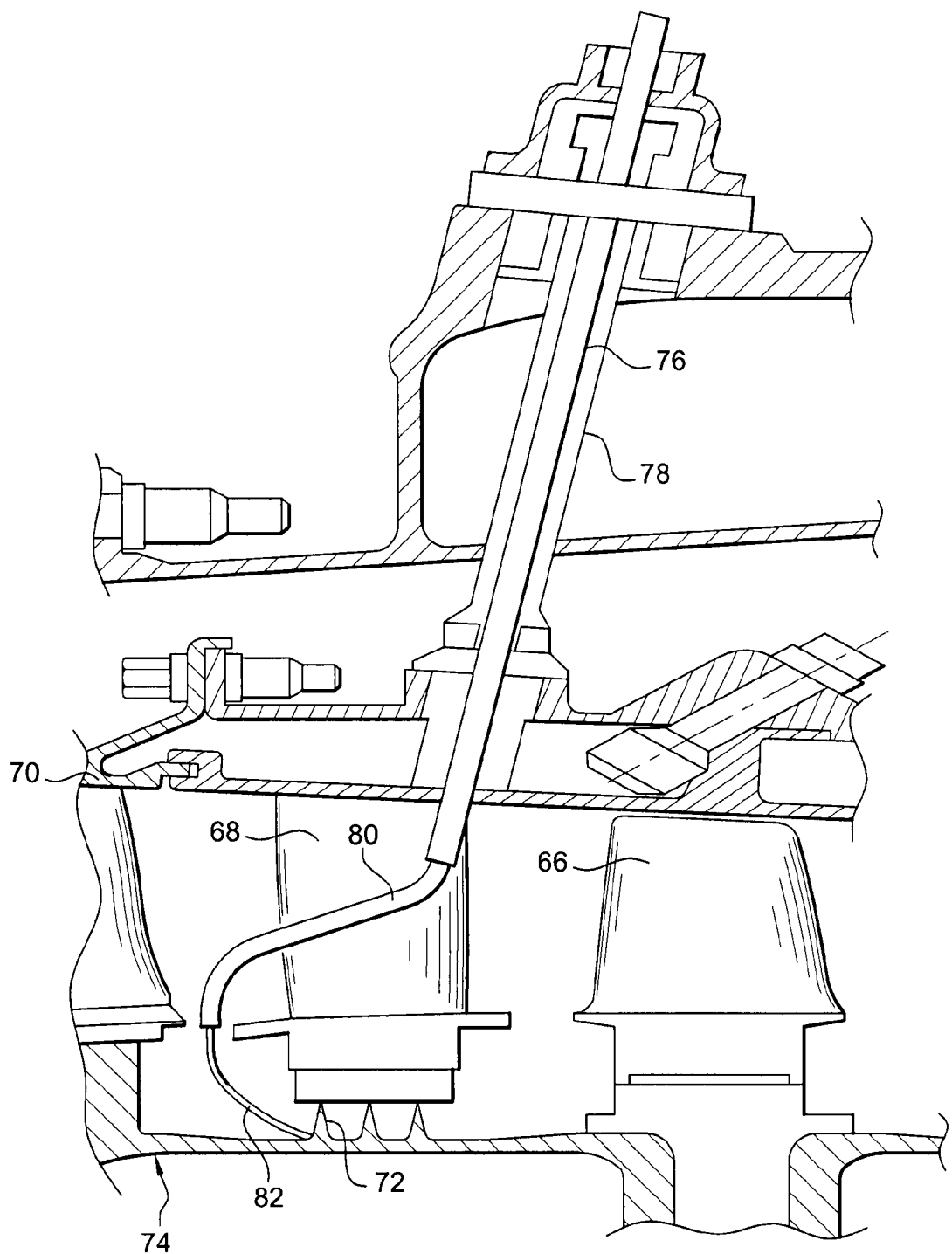
FIG. 12 is a diagrammatic axial section view of a portion of a turbomachine that is to be investigated with the help of a steerable structure of the invention.

FIG. 12 shows a stage of a turbomachine including an alternation of moving blades 66 and stationary vanes 68 surrounded by an outer casing 70. The stationary vanes 68 have their radially inner ends in alignment with wipers 72 mounted on a portion of the rotor 74. These wipers 72 serve to prevent any air flowing between a stationary vane 68 and the rotor 74. It is therefore important to be able to inspect the wear state of these parts in order to avoid any decrease in the performance of the turbomachine.

The catheters or endoscope used for this purpose are of the telescopic type, i.e. they are made up of a plurality of elastically deformable bodies fitted with contractile actuators and engaged one in another.

A catheter of the invention can be used to inspect these wipers 72 quickly and simply. To do this, a first tubular rigid body 76 is inserted in an endoscopic orifice 78 that opens out between two adjacent stationary vanes 68, and an S-shaped second flexible body 80 is inserted within the first body. The actuator heater means enable the catheter 80 to be shaped within the space between two stationary vanes 68. Finally, a third flexible body 82 possessing only one direction of curvature is inserted inside the first two catheters 78 and 80 and is controlled so that its head can be put into contact with a wiper 72. The rotor of the turbomachine is then turned so as to enable non-destructive inspection means placed in the head of the catheter 82 to examine the surface state of the part over 360°. The head may be connected to a spring as described above in order to ensure continuous contact.

The total length of the catheter is quite long, for example about 60 cm, and this can lead to errors in positioning its distal end. The stationary vanes 68 can be used as bearing and hanging points for the intermediate catheter 80 with the help of elements such as clips or deployable meshes for stabilizing the telescopic catheter as a whole.

The variable stiffness configuration enables the catheter to be moved up to zones that are difficult to access and that require the catheter to be passed along passages of small dimensions.

Catheters of elongate cross-section may be solid as shown in the drawings or they may be hollow. With solid telescopic catheters, it is possible to provide guide means such as rails situated along the longitudinal bodies.

In the various embodiments described, it is possible to have various numbers of SMA or contractile wires and various numbers of extra thickness layers in order to obtain profiles of desired curvature.

The invention is not limited to SMA type actuators as used in the embodiments shown in the drawings, i.e. single-acting SMA wires, that can act in only one direction. It is also possible to use other actuators such as SMA blades, optionally having memory of two positions so as to enable the steerable structure to return more quickly to its initial state. It is also possible to envisage producing a return to the initial more quickly by placing SMA wires along the elastic body and in an opposing position, and then actuating the wires in succession.

Although the invention described above is particularly useful in the field of three-dimensional investigation of complex industrial apparatus, it can also be used in other fields, and in particular in the biomedical field where the steerability of catheters is a key feature in successful anatomical and functional investigation.

The invention also relates to a catheter or endoscope including automatic control means connected to each of its contractile actuators. This is particularly advantageous for use with systems of accurately known geometry. By using the plans of the system, it is possible to define accurately the path that is to be followed and the shape that is given to the structure, and to program control of its actuators starting from the structure being inserted into an endoscopic orifice.

Because of the simplicity with which the invention can be implemented and because of its low cost, it is possible to fabricate catheters that are dedicated to investigating systems of a given type and to performing non-destructive inspection of parts of a single type only.

It is thus possible to optimize the fabrication of a steerable structure of the invention as a function of the zone and the type of non-destructive inspection it is to perform, thereby achieving a significant improvement in performance for the user.

The contractile material may for example be an alloy of nickel and titanium. The flexible body and the layers of material may be made of spring steel or of a polymer such as polyethyl ether ketone, epoxy resin, polyethylene, or polyurethane depending on the stiffness desired.

The invention is not limited to catheters of rectangular or circular section and it applies equally well to catheters of arbitrary cross-section, e.g. oval, square, triangular, etc.

What is claimed is:

1. A steerable structure of catheter or endoscope type for observing or treating a masked object, the structure comprising:
    an elastically deformable longitudinal body having at least one actuator of shape memory type material incorporated longitudinally in the longitudinal body together with Joule-effect heater means enabling the actuator to be contracted longitudinally so as to cause the longitudinal body to bend,
    wherein the actuator extends over at least one portion of the longitudinal body of a varying stiffness comprising at least one extra thickness of material, said portion of the longitudinal body being formed with at least one extra thickness varying the thickness of the body over said portion and said varying stiffness resulting from said extra thickness.

2. The structure according to claim 1, wherein the varying stiffness of the longitudinal body is designed so that contraction of the actuator modifies and/or inverts the longitudinal or transverse curvature of the longitudinal body.

3. The structure according to claim 1, wherein the longitudinal body comprises at least one tube.

4. The structure according to claim 3, wherein the actuator extends longitudinally over an inside wall or an outside wall of the tube.

5. The structure according to claim 3, wherein the tube has a diameter of the order of 2 mm to 6 mm.

6. The structure according to claim 1, wherein the longitudinal body comprises a blade of elongate cross-section.

7. The structure according to claim 6, wherein two parallel actuators are incorporated in the blade and extend along a longitudinal face of the blade.

8. The structure according to claim 6, wherein the blade has a thickness ranging between 1 mm to 2 mm, a width of 1 cm, and a length ranging between 5 to 10 cm.

9. The structure according to claim 1, wherein the actuator is a wire.

10. The structure according to claim 9, wherein the diameter of the wire ranges between 0.1 mm to 0.5 mm.

11. The structure according to claim 1, wherein the portion of varying stiffness and the extra thickness of material are made of polymer.

12. The structure according to claim 1, wherein the actuator is made of an alloy of titanium and nickel.

13. The structure according to claim 1, wherein the structure is of the telescopic type consisting in a plurality of elastically individual deformable bodies that are provided with actuators and that are engaged one in another.

14. The structure according to claim 13, wherein the distal end is linked to a head provided with non-destructive inspection means via resilient means adapted to exert a longitudinal thrust on the head when the head is brought into contact with a surface.

15. The structure according to claim 14, wherein the resilient means are helical springs.

16. The structure according to claim 15, wherein the springs are made of shape memory type material and are connected to Joule-effect heater means.

17. The structure according to claim 14, wherein the non-destructive inspection means are Foucault current probes or ultrasound probes.

18. The structure according to claim 13, wherein one of the transverse dimensions of the structure varies from 8 mm at the proximal end to 1 mm at the distal end.

19. The structure according to claim 1, wherein the structure comprises means for hanging on or bearing against surrounding stationary elements.

20. The structure according to claim 1, wherein the heater means are connected to automatic control means.

* * * * *